United States Patent
Ohno

(10) Patent No.: US 10,232,483 B2
(45) Date of Patent: Mar. 19, 2019

(54) ULTRASONIC DISPLACEMENT SENSOR AND WORKPIECE IDENTIFICATION APPARATUS INCLUDING THE SAME

(71) Applicant: Tokyo Seimitsu Co., Ltd., Tokyo (JP)

(72) Inventor: Yoshiki Ohno, Ibaraki (JP)

(73) Assignee: Tokyo Seimitsu Co., Ltd., Tokyo (JP)

(*) Notice: Subject to any disclaimer, the term of this patent is extended or adjusted under 35 U.S.C. 154(b) by 0 days.

(21) Appl. No.: 15/765,477

(22) PCT Filed: Dec. 28, 2016

(86) PCT No.: PCT/JP2016/089027
§ 371 (c)(1),
(2) Date: Apr. 2, 2018

(87) PCT Pub. No.: WO2017/119380
PCT Pub. Date: Jul. 13, 2017

(65) Prior Publication Data
US 2018/0297165 A1    Oct. 18, 2018

(30) Foreign Application Priority Data

Jan. 5, 2016 (JP) ................................ 2016-000522
Jan. 5, 2016 (JP) ................................ 2016-000609

(51) Int. Cl.
*G01B 17/00* (2006.01)
*G01S 15/10* (2006.01)
(Continued)

(52) U.S. Cl.
CPC ........... *B23Q 17/006* (2013.01); *B23Q 17/00* (2013.01); *G01B 17/00* (2013.01);
(Continued)

(58) Field of Classification Search
CPC ......... B23Q 17/00; G01B 17/00; G01S 15/10; G01S 17/026; G01S 17/88; G01S 7/4813
(Continued)

(56) References Cited

U.S. PATENT DOCUMENTS

2008/0110265 A1   5/2008   Wong
2008/0165620 A1   7/2008   Sugiura

FOREIGN PATENT DOCUMENTS

DE    102006033693 A1    2/2007
JP    H03229111 A        10/1991
(Continued)

OTHER PUBLICATIONS

International Search Report dated Mar. 14, 2017 filed in PCT/JP2016/089027.
(Continued)

*Primary Examiner* — J M Saint Surin
(74) *Attorney, Agent, or Firm* — Rankin, Hill & Clark LLP

(57) ABSTRACT

Provided is an ultrasonic displacement sensor that more accurately identifies a plurality of models on a conveyance line on which a plurality of types of workpieces having different specifications coexists, in particular, on a conveyance line of cylinder blocks in a manufacturing facility of engines for automobiles, to thereby improve reliability. An ultrasonic displacement sensor 1 or 2 for transmitting ultrasonic waves to an object, receiving reflected waves, and measuring time between transmission and reception includes: a main body case 41 including an ultrasonic element 31 or 32 at an end; a transparent case 42 attached to the main body case 41; a photoreflector 44 provided at a position of the transparent case 42 and including a light emission portion and a light reception portion; and a switching unit configured to switch, on the basis of output from the (Continued)

photoreflector 44, between an installation mode in which an attachment position of the main body case 41 is adjusted and a measurement mode in which the object is measured.

11 Claims, 14 Drawing Sheets

(51) Int. Cl.
*B23Q 17/00* (2006.01)
*G01S 17/02* (2006.01)
*G01S 17/88* (2006.01)
*G01S 7/481* (2006.01)
*G01S 7/52* (2006.01)
*G01S 7/521* (2006.01)
*G01S 15/87* (2006.01)
*G01S 15/88* (2006.01)
*G01N 29/44* (2006.01)

(52) U.S. Cl.
CPC ........ *G01N 29/4454* (2013.01); *G01S 7/4813* (2013.01); *G01S 7/521* (2013.01); *G01S 7/52004* (2013.01); *G01S 15/10* (2013.01); *G01S 15/87* (2013.01); *G01S 15/88* (2013.01); *G01S 17/026* (2013.01); *G01S 17/88* (2013.01)

(58) Field of Classification Search
USPC .......................................................... 73/579
See application file for complete search history.

(56) References Cited

FOREIGN PATENT DOCUMENTS

| | | |
|---|---|---|
| JP | H06160971 A | 6/1994 |
| JP | H07004908 A | 1/1995 |
| JP | H08287175 A | 11/1996 |
| JP | H10255578 A | 9/1998 |
| JP | 2004294095 A | 10/2004 |
| JP | 2006292634 A | 10/2006 |
| JP | 2008119786 A | 5/2008 |

OTHER PUBLICATIONS

Office Action dated Jul. 9, 2018 for the corresponding German Patent Application No. 112016004651.0; English translation.

200mm → 196.5 (mm/+10°C)

SUFFICIENT TIME TO PREVENT INTERFERENCE

ULTRASONIC DISPLACEMENT SENSOR AND WORKPIECE IDENTIFICATION APPARATUS INCLUDING THE SAME

TECHNICAL FIELD

The present invention relates to an ultrasonic displacement sensor that identifies workpieces on a conveyance line or the like by using sonic waves as a medium and a workpiece identification apparatus including the same.

BACKGROUND ART

In recent years, demand for specifications of products from customers has been diversified. In order to satisfy this diversified demand, there have been increased cases where specifications of products are differentiated for respective destinations of the products. In addition, in order to satisfy users' desires, new models have been added and the number of types of products has been increasingly grown.

Therefore, it is necessary to manufacture various types of models in a small amount (perform high-mix low-volume production) without reducing a rate of operation, by altering typical equipment that has performed low-mix high-volume production.

There are various tasks to mixedly manufacture various types of products in a typical equipment (line). The most conspicuous task is to correctly determine a plurality of types of workpieces moving down the line (e.g., assembly line) to thereby unmistakably execute assembly work or processing work different for each type of product.

For example, there is a conveyance line of cylinder blocks, which are castings or the like, in a manufacturing facility of engines for automobiles. A plurality of types of cylinder blocks serving as workpieces mixedly moves on this conveyance line in many cases. Therefore, it is necessary to identify types of cylinder blocks and sort the cylinder blocks according to the types at an entrance or exit of the conveyance line. In addition, it is known that the following identification methods are generally used, instead of a contact-type displacement sensor. Specifically, a barcode, which is a protruding portion, is formed on a casting or the like moving down the conveyance line. This barcode is obliquely irradiated with light from a light emitting source, and therefore a shadow of this barcode is formed. Then, an image of this shadow is captured by a TV camera and predetermined information processing is performed, and therefore, the type of the casting or the like is identified.

Further, the following detection method is also carried out. A barcode, which is a protruding portion, is integrally casted with a reference bar on a circumference surface of a cylinder block that is a casting serving as a target to be identified. A model number, a mold number, and the like are expressed by the number of protruding portions and intervals therebetween. The model number, the mold number, and the like are detected by a TV camera.

Further, as disclosed in, for example, Patent Literature 1, the following technology is also known. In order to reduce the number of integrally casted protruding portions, in other words, reference bars, a casting or the like is identified by obtaining widths and heights of the bars. A plurality of types of castings or the like is identified by changing the heights or the widths of the bars for each type of casting or the like.

Further, as disclosed in, for example, Patent Literature 2, the following technology is also known. In order to correctly identify various types of workpieces fed into a conveyor, a distance from a surface of a workpiece and presence/absence of a blind bore on the surface of the workpiece and a position thereof are obtained by a displacement laser sensor serving as an optical measurement device.

Further, as disclosed in, for example, Patent Literature 3, the following technology is also known. By optically examining an external form without contact, instead of using a contact-type displacement sensor, highly accurate detection is carried out without receiving a harmful influence such as a positional shift of a workpiece.

Further, as disclosed in, for example, Patent Literature 4, the following technology is also known. In an ultrasonic sensor, a reflection amount or transmission amount of ultrasonic waves is different depending on a material of an object. In order to avoid false detection caused by this fact and achieve stable detection, a distance calculation unit calculates a distance from an object on the basis of time between a timing at which ultrasonic waves are emitted and a timing at which reflected waves are detected. The type of the object is detected on the basis of the calculated distance and a receiving amount received by an ultrasonic wave transmission and reception unit.

Further, as disclosed in, for example, Patent Literature 5, the following technology is also known. A photoreflector is used as a release switch of a camera in order to achieve releasing of a camera without contact and reduce an influence of camera shake caused by release operation.

CITATION LIST

Patent Literature

PATENT LITERATURE 1: JP-A-8-287175
PATENT LITERATURE 2: JP-A-2008-119786
PATENT LITERATURE 3: JP-A-2004-294095
PATENT LITERATURE 4: JP-A-2006-292634
PATENT LITERATURE 5: JP-A-6-160971

SUMMARY OF INVENTION

Problems to be Solved by the Invention

In the above related arts, in a case where workpieces are identified by contact on a conveyance line of assembly or processing, it is difficult to carry out highly accurate detection because of a positional shift or the like of the workpieces. In addition, there is also a possibility of a malfunction or breakage caused by a shock. Therefore, those technologies are not realistic.

Further, in a case of using an optical TV camera or an optical displacement laser sensor, the optical TV camera or displacement laser sensor is influenced by an environment in which the conveyance line is placed. For example, it is necessary to identify a model immediately before processing in a machine tool such as a machining center. This machining center has an automatic tool-exchanging function and carries out different types of processing such as milling, boring, punching, and tapping depending on a purpose. However, in an environment including microparticles such as oil mist and dust, light or laser is diffused due to an influence thereof in the optical one. Therefore, it is difficult to achieve accurate identification. Thus, it is extremely difficult to identify a large number of models.

Further, in a case where an eddy-current displacement sensor which uses a high-frequency magnetic field and is resistant to dust, water, oil, and the like is used, accuracy and a speed of response are fast, whereas a measurable distance is short, i.e., approximately several millimeters. Therefore, the eddy-current displacement sensor is not suitably used in the conveyance line of the machining center or the like.

Further, in a case where an ultrasonic displacement sensor using sonic waves as a medium is used, a measurement distance is long. Therefore, this ultrasonic displacement sensor is suitably used in the conveyance line. However, when this ultrasonic displacement sensor is simply used, accuracy is lower than that of other methods. Further, a size of a surface to be measured is inevitably increased. Therefore, in order to identify a large number of models, it is necessary to increase a surface to be measured of a workpiece accordingly.

In particular, in a case where a large number of models are identified by the ultrasonic displacement sensor, the large number of models are identified by using time of arrival of ultrasonic waves reflected by a surface of a workpiece. Therefore, a threshold is defined for each model and time of arrival is compared with this threshold, and thus a rank is identified.

Further, in the technology disclosed in Patent Literature 4, a threshold of a receiving amount and a threshold of a distance are simply set in a setting unit in advance as thresholds, and identification is carried out. Therefore, it is not considered that time of arrival varies depending on a measurement environment. Thus, even in a case where each threshold is specified as a certain value or a range of each threshold is set, it is difficult to identify a large number of models depending on a measurement environment such as temperature in particular. In particular, when a range of values serving as a threshold is simply set to allow variation, this threshold includes an excessive margin. In that case, when a plurality of models is identified, the number of identifiable models needs to be small.

Further, in a case where workpieces are identified by the ultrasonic displacement sensor in the conveyance line, it is necessary not only to set a threshold but also to adjust an attachment position of a main body of the ultrasonic displacement sensor, such as a position and a direction thereof, before setting. This adjustment is more difficult as the number of models is increased. Then, after position adjustment and installation thereof, measurement is carried out. At this time, in an installation mode, the ultrasonic displacement sensor needs to output nothing to the setting unit of thresholds or a measurement unit. Therefore, it is necessary to provide a switch for switching the ultrasonic displacement sensor itself from the installation mode to a measurement mode.

In a case where a mechanical switch is simply attached to the ultrasonic displacement sensor, a position thereof may be shifted even when the mechanical switch can be positioned and attached to increase a reception intensity of ultrasonic waves. This is because a shock generated when the switch is operated is transmitted. In view of this, a photoreflector is suitably used as the switch as disclosed in Patent Literature 5. However, when the photoreflector is simply provided in the main body of the ultrasonic displacement sensor, it is impossible to identify whether or not position adjustment is completed. Further, a countermeasure for dust and the like is important to use the photoreflector in the conveyance line.

An object of the present invention is to solve the problems of the above related arts. Further, an object of the present invention is to, even in a case where a large number of models as workpieces mixedly move down a conveyance line of assembly or processing, securely identify types of the respective models at an entrance or exit of the conveyance line. An object of the present invention is to identify a large number of models on, in particular, a conveyance line of cylinder blocks in a manufacturing facility of engines for automobiles and more accurately carry out work of processing changed for each model and work of sorting cylinder blocks according to each model, thereby improving reliability.

Solutions to the Problems

In order to achieve the above object, the present invention includes an ultrasonic displacement sensor for transmitting ultrasonic waves to an object, receiving reflected waves of the ultrasonic waves, and measuring time between transmission and reception, the ultrasonic displacement sensor including: a main body case including an ultrasonic element at an end; a transparent case attached to the main body case; a photoreflector provided at a position of the transparent case and including a light emission portion and a light reception portion; and a switching unit configured to switch between an installation mode in which an attachment position of the main body case is adjusted and a measurement mode in which the object is measured on the basis of output from the photoreflector.

In the above described ultrasonic displacement sensor, it is desirable to include an LED configured to be turned on to have a light amount based on an intensity of received reflected waves.

In the above described ultrasonic displacement sensor, it is desirable to include an ultrasonic element configured to transmit ultrasonic waves and receive reflected waves when the light reception portion accepts input, and an intensity detection unit configured to detect an intensity of received reflected waves.

In the above described ultrasonic displacement sensor, it is desirable that the transparent case is attached to the main body case via a packing.

In the above described ultrasonic displacement sensor, it is desirable that the transparent case is provided at another end that is an opposite side of the end at which the ultrasonic element is placed.

In order to achieve the above object, the present invention includes a workpiece identification apparatus for identifying a model of a workpiece placed on a conveyance line and having a portion to be identified at a predetermined position, the workpiece identification apparatus including: a master sensor and a slave sensor configured to transmit ultrasonic waves to the portion to be identified, receive reflected waves, and measure time between transmission and reception; a master sensor and a slave sensor, the master sensor and the slave sensor including a main body case including an ultrasonic element at an end, a transparent case attached to the main body case, and a photoreflector provided at a position of the transparent case and including a light emission portion and a light reception portion; and a switching unit configured to switch between an installation mode in which an attachment position of the main body case is adjusted and a measurement mode in which the workpiece is measured on the basis of output from the photoreflector.

In the above described workpiece identification apparatus, it is desirable to include an LED configured to be turned on to have a light amount based on an intensity of received reflected waves.

In the above described workpiece identification apparatus, it is desirable that the master sensor and slave sensor include an LED configured to be turned on to have a light amount based on an intensity of received reflected waves.

In the above described workpiece identification apparatus, it is desirable to include an ultrasonic element configured to transmit ultrasonic waves and receive reflected waves when the light reception portion accepts input, and an intensity detection unit configured to detect an intensity of received reflected waves.

In the above described workpiece identification apparatus, it is desirable that the master sensor and the slave sensor are arranged at a position facing the portion to be identified and identify the model by detecting a difference in level between a surface of the portion to be identified facing the master sensor and a surface of the portion to be identified facing the slave sensor.

Advantageous Effects of the Invention

According to the present invention, a transparent case attached to a main body case in which an ultrasonic element is placed and a photoreflector provided at a position of the transparent case are provided. An installation mode in which an attachment position of the main body case is adjusted and a measurement mode in which an object is measured are switched on the basis of output from the photoreflector. Therefore, in a case where positioning is carried out in such a manner that a reception intensity of ultrasonic waves in the installation mode is increased, the position is not shifted when the mode is switched to the measurement mode after positioning. This makes it possible to securely identify a large number of models of workpieces. In particular, it is possible to accurately identify a plurality of models, particularly on a conveyance line of cylinder blocks in a manufacturing facility of engines for automobiles, thereby improving reliability.

BRIEF DESCRIPTION OF THE DRAWINGS

FIG. 1 is a configuration diagram in which a workpiece identification apparatus according to an embodiment of the present invention is applied to a machine tool or the like.

DESCRIPTION OF EMBODIMENTS

Hereinafter, embodiments of the present invention will be described in detail with reference to the drawings.

In production of automobiles, high-mix low-volume production is desired to satisfy diversification of consumers' needs for automobiles. In such high-mix low-volume production, it is preferable to assemble products in a various-model mixing line compatible with a large number of models, as compared with assembling products in a line dedicated to each model, in view of production efficiency, the whole length of the line, cost of supplementary equipment, a rate of operation in the line, and the like. However, the type of work required to assemble products, man-hours of work required to complete products, time required to perform each work, and the like are greatly different depending on models.

Figure 1:
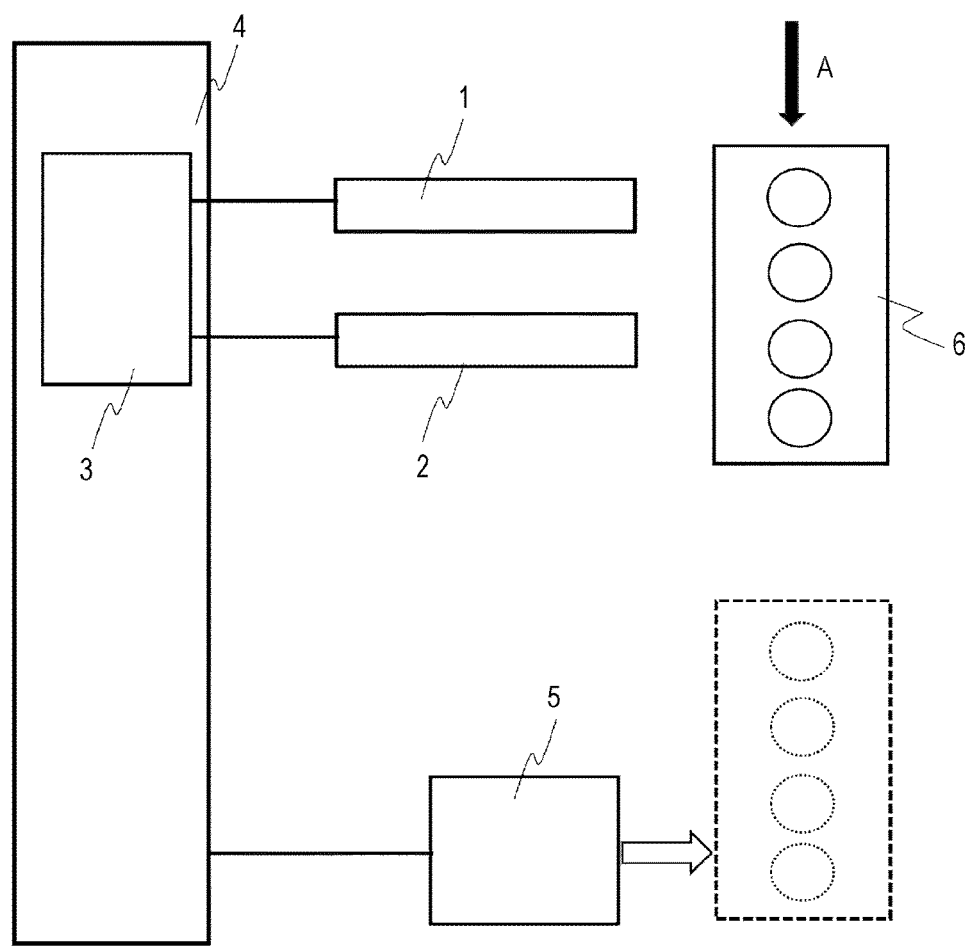

FIG. 1 is a configuration diagram in which a workpiece identification apparatus according to an embodiment is applied to a machining center that is a machine tool. A workpiece 6 is a cylinder block. This cylinder block includes a plurality of pistons. A crankshaft is attached to a crankcase portion in a lower portion of the cylinder block.

Cast iron or a casting made of aluminum alloy is generally used as the cylinder block. Various types of workpieces 6 are mixedly fed into a conveyance line. A conveyance line of cylinder blocks is provided in a manufacturing facility of engines for automobiles. A plurality of types of cylinder blocks serving as workpieces mixedly moves down this conveyance line in many cases. Therefore, a model, which is a type of a cylinder block, needs to be identified at an entrance or exit of the conveyance line.

Further, the machining center is a numerical control machine tool that carries out various types of processing such as milling, punching, boring, and tapping without changing attachment of workpieces. In FIG. 1, for example, a reference sign 5 denotes a machine tool that carries out punching processing. Further, a large number of cutting tools stored in a tool magazine automatically carry out processing in response to a command of computer numerical control. This machine tool includes an automatic tool-exchanging device. Further, there are known a machine tool that can rotate a machining table at a high speed and carry out turning by using a tool bite attached to a main shaft, a machine tool using a grinding stone instead of a milling tool, and a machine tool including a probe for measuring dimensions. A main purpose is processing. Therefore, microparticles such as oil mist and dust exist in an environment in which the machining center is installed. In order to identify castings such as cylinder blocks in such an environment, an ultrasonic displacement sensor is desirably used.

A cylinder block, which is the workpiece 6, is placed on the conveyance line. This cylinder block is conveyed in a direction of an arrow A and is stopped. Reference signs 1 and 2 denote ultrasonic displacement sensors. The reference sign 1 denotes a master sensor. The reference sign 2 denotes a slave sensor. Ultrasonic waves are transmitted to a portion to be identified provided at a predetermined position of the workpiece 6 at a position at which the workpiece 6 is stopped. A model is identified by using received reflected waves.

A reference sign 3 denotes a sensor unit that carries out measurement and identification using the master sensor 1 and the slave sensor 2. This sensor unit receives an instruction to start measurement from a machine tool controller 4 and transmits an identification result. The machine tool controller 4 receives the identification result and then issues an instruction to move the workpiece 6 to a processable position shown by a broken line. Then, the machine tool controller 4 issues an instruction for carrying out processing to a machine tool 5, the instruction depending on the identification result, namely, the model that is received from the sensor unit 3. For example, the instruction on processing relates to a size, a position, and the like of a hole serving as specifications in punching processing and relates to a rotation speed and the like serving as processing conditions.

Herein, ultrasonic waves have an excellent converging property and excellent directionality. Further, ultrasonic waves are compressional waves of air. Therefore, an influence of scattering of microparticles in the air is small, as compared with a case of optical one. Thus, it is possible to carry out stable measurement even in an environment of oil mist and dust in which the machine tool 5 is installed. Further, by using ultrasonic waves, it is possible to measure various materials such as metal, wood, glass, rubber, powder, and liquid as an object to be measured (workpiece 6) without contact. In addition, it is possible to carry out measurement even in a distant place, i.e., a place that is several hundreds of millimeters away from the workpiece 6.

The ultrasonic displacement sensor detects presence/absence of an object and a distance from the object by causing a transmitter to send ultrasonic waves to the object and causing a receiver to receive reflected waves thereof. An ultrasonic element is used to send and receive ultrasonic waves. The ultrasonic element is an element that generates ultrasonic waves by using applied electric energy or an element that converts ultrasonic wave oscillation energy into electric signals. The ultrasonic sensor can normally be a barium titanate oscillator using a piezoelectric phenomenon.

When an AC voltage is applied to the piezoelectric element, the element oscillates. This element has an inherent oscillation frequency. By applying an AC voltage of the same frequency as the frequency, the element efficiently oscillates. Generally, a piezoelectric element of 40 kHz is used in many cases. A piezoelectric element of a low frequency is used to measure a long distance. A piezoelectric element of a high frequency is used to accurately measure a short distance.

Further, the ultrasonic displacement sensor can measure various materials such as metal, wood, glass, rubber, powder, and liquid. Further, measurement is carried out without contact. Therefore, there is no influence of viscosity. In addition, there is no problem of corrosion. The ultrasonic displacement sensor has the following characteristics. Specifically, this sensor can carry out detection in a long distance and therefore does not hinder movement of a moving object on the conveyance line. This sensor can stably measure a level in a bad environment.

Further, the ultrasonic displacement sensor measures a length by measuring time between transmission of sonic waves and reception thereof. Thus, even in a case where a surface of an object to be measured is rough or strength thereof is changed, time of arrival is not changed in the ultrasonic displacement sensor. Thus, measurement is not influenced by surface roughness, which is different from the optical one. This makes it possible to carry out stable measurement. This advantage can be used in a case where the workpiece 6 is, in particular, a cylinder block that is a casting. Further, measurement is not influenced by a hot cylinder block.

Further, a speed of sound in the air changes depending on temperature. Therefore, a measurement result of the ultrasonic displacement sensor is influenced by a change in atmosphere. In view of this, both the master sensor 1 and the slave sensor 2 are ultrasonic displacement sensors that measure time between transmission and reception. In this way, the sensor unit 3 carries out identification by using a difference between values measured by a pair of the master sensor 1 and slave sensor 2.

A model is identified by using the difference between the values measured by the master sensor 1 and the slave sensor 2. This makes it possible to offset an influence of temperature, oil mist, dust, and the like in a distance from the master sensor 1 and the slave sensor 2 to the portion to be identified of the workpiece 6. Thus, also in an environment such as a manufacturing line of cylinder blocks, it is possible to accurately identify a large number of models in a sufficient operation distance to the extent that processing is not hindered.

Figure 2:
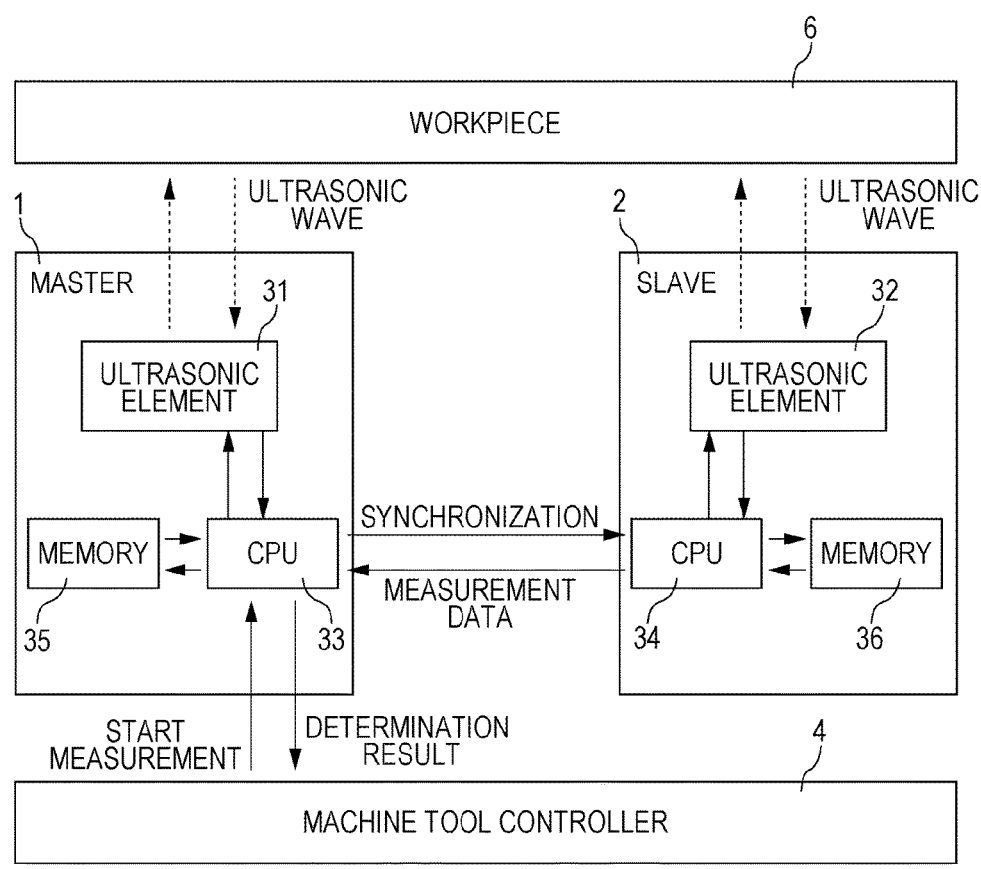
FIG. 2 is a block diagram of identification processing in an embodiment.
Figure 3:
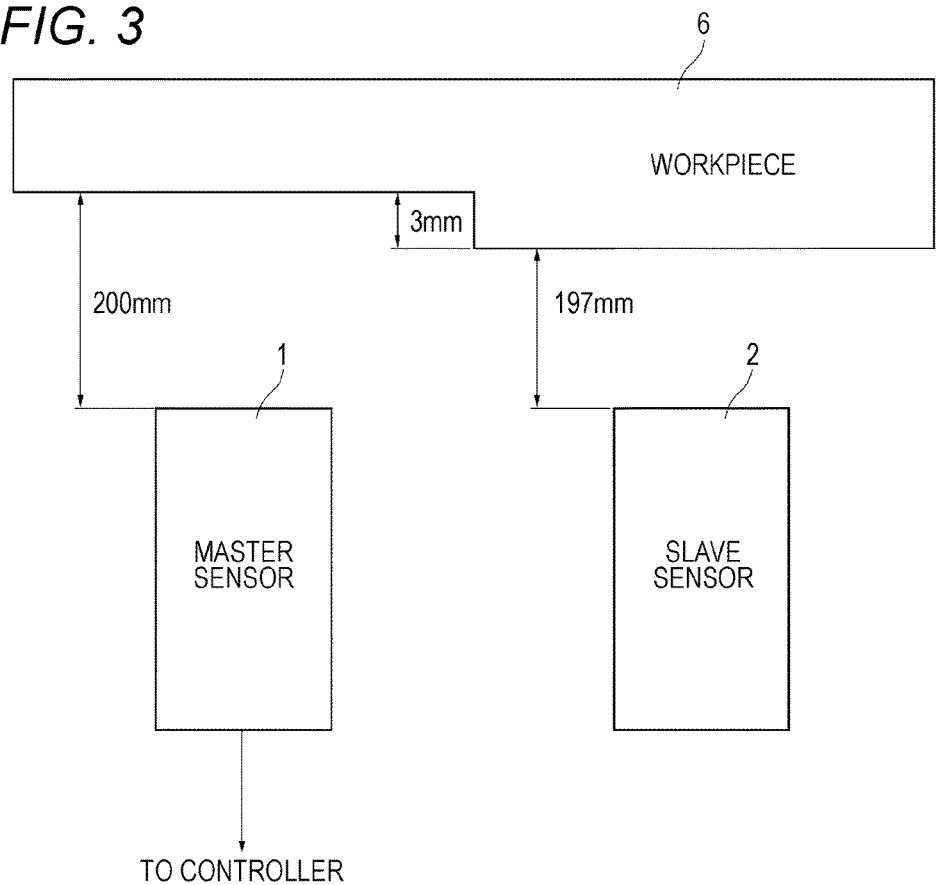
FIG. 3 is an explanatory view of an identification shape of a workpiece and processing in an embodiment.

FIG. 2 is a block diagram of identification processing. Both the master sensor 1 and the slave sensor 2 are configured to measure a distance to the workpiece 6. FIG. 3 illustrates a shape of the portion to be identified that is a surface to be measured of the workpiece 6. The shape of the portion to be identified is integrally formed with the workpiece 6. There is a difference in level between a surface facing the master sensor 1 and a surface facing the slave sensor 2. Unevenness thereof is several millimeters.

In a case of measurement, the surface to be measured needs to face the master sensor 1 and the slave sensor 2 at a stop position of the workpiece 6 as illustrated in FIG. 3. A size of the surface to be measured is determined on the basis of stop-position accuracy and a beam size of the ultrasonic displacement sensors. Note that reduction in area to be measured is required because the cylinder block is a casting. The portion to be identified has a difference in level, and therefore a measurement range becomes clear. As a result, it is possible to identify a larger number of models.

Further, the difference between the values measured of the master sensor 1 and the slave sensor 2 is used, whereby a distance of length measurement between the sensors and the workpiece 6 is offset. With this, measurement is limited to measurement of the unevenness. Further, when two ultrasonic sensors are simply arranged side by side and are used, sonic waves interfere with each other. This causes a measurement error. On the contrary, the master sensor 1 and the slave sensor 2 alternately transmit ultrasonic waves so as to avoid interference. This makes it possible to prevent ultrasonic waves of the master sensor 1 and the slave sensor 2 from interfering with each other.

As illustrated in FIG. 2, the master sensor 1 and the slave sensor 2 have a similar configuration. The master sensor 1 and the slave sensor 2 include ultrasonic elements 31 and 32, respectively. The master sensor 1 and the slave sensor 2 are switched by CPUs 33 and 34 to carry out transmission and reception. Memories 35 and 36 temporarily store measurement data. Storage and reading of this measurement data are controlled by the CPUs 33 and 34. The master sensor 1 and the slave sensor 2 are connected to each other. The ultrasonic element 32 of the slave sensor 2 oscillates to synchronize with clock signals generated by the master sensor 1. The measurement data of the slave sensor 2 is transmitted to the CPU 33 of the master sensor 1. With this, even in a case where measurement is carried out many times, a transmission timing of ultrasonic waves is not shifted. Further, interference can be avoided for a long time.

The configuration illustrated in FIG. 2 is an example. It is possible to employ any configuration as long as the configuration exhibits a similar function. For example, it is also possible to employ a configuration that controls the master sensor 1 and a master sensor 2 by using a single CPU, instead of a configuration including two CPUs, i.e., the CPUs 33 and 34. Further, there may be employed a configuration that operates the master sensor 1 and the master sensor 2 by using a single memory.

The CPU 33 of the master sensor 1 is connected to the machine tool controller 4. An instruction to start measurement is issued by the machine tool controller 4. An identification result is transmitted from the CPU 33 to the machine tool controller 4. The machine tool controller 4 receives the identification result and then moves and stops the workpiece 6. Then, the machine tool controller 4 instructs the machine tool 5 to carry out processing based on the identification result.

The master sensor 1 and the slave sensor 2 operate as follows to avoid interference. The master sensor 1 generates a clock signal serving as a reference time for transmitting ultrasonic waves. The slave sensor 2 transmits ultrasonic waves so as to synchronize with the clock signal generated in the master sensor 1. In this way, the master sensor 1 and the slave sensor 2 alternately oscillate. As an oscillation interval and a transmission interval, sufficient time to eliminate reverberation caused by reflected waves from the workpiece 6 is set. The reverberation caused by reflected waves depends on an operation distance from the master sensor 1 and the slave sensor 2 to the workpiece 6. Therefore, the operation distance is determined by setting the sending (transmission) interval.

Measurement is started as follows. First, ultrasonic waves are sent from the ultrasonic element 31 of the master sensor 1. Then, ultrasonic waves are sent from the ultrasonic element 32 of the slave sensor 2. Those are defined as a single set. A predetermined number of sets are repeated, and then sending is stopped. As illustrated in FIG. 3, the identification shape of the surface to be measured of the workpiece 6 is a pattern shape of unevenness provided on the surface. In the example of FIG. 3, a distance from the master sensor 1 to the workpiece 6 is 200 mm as the operation distance, and a distance from the slave sensor 2 to the workpiece 6 is 197 mm. The slave sensor 2 side of the identification shape has a difference in level protruding toward the ultrasonic displacement sensor by 3 mm.

In view of a measurement error or the like, a value of the difference in level is desirably approximately 1/40 to 1/200 of the operation distance. With this, even in a case where a large number of models are identified, it is possible to secure resolution of the sensor. Ultrasonic waves are transmitted from the ultrasonic element 31 of the master sensor 1. Time until reflected waves from a recessed portion of the workpiece 6 arrive at the master sensor 1 is counted as measurement data and is stored in the memory 35. Next, a timing is shifted to avoid interference, and ultrasonic waves are transmitted from the ultrasonic element 32 of the slave sensor 2. Time until reflected waves return to the slave sensor 2 is counted and is stored in the memory 36.

After sending is stopped, the slave sensor 2 outputs the stored measurement data to the master sensor 1. The master sensor 1 calculates a difference between the measurement data of the master sensor 1 stored in the memory 35 and the measurement data output from the slave sensor 2. Then, the CPU 33 of the master sensor 1 determines that the slave sensor 2 side protrudes by 3 mm as a pattern of the surface to be measured.

Figure 4:
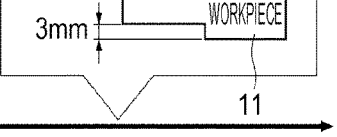
FIG. 4 is an explanatory view of allocation (mastering) of workpiece numbers in an embodiment.

FIG. 4 is an explanatory view of a mode (mastering mode) in which workpiece numbers are allocated and a threshold serving as a reference of identification is stored in the memory 35. Necessary types of master workpieces 11 are additionally prepared. Those master workpieces 11 are references of a cylinder block serving as an actual target to be measured placed on a conveyance line. The master workpiece 11 is set in front of the master sensor 1 and the slave sensor 2. A master workpiece 11 corresponding to a workpiece number 1 is placed on a conveyance line of a workpiece serving as actual target to be measured. A measurement unit measures the master workpiece 11. A differential value between values read by the master sensor 1 and the slave sensor 2 is stored. This differential value is associated with the workpiece number 1. Then, a pattern shape of the master workpiece 11 is registered as the workpiece number 1 in an identification data table 12 serving as a reference of identification as illustrated in the drawing. The identification data table 12 is stored in the memory 35 of the master sensor 1 as a table structure.

Further, time of arrival varies depending on a measurement environment. Therefore, the measurement unit measures the master workpiece 11 corresponding to each workpiece number a plurality of times. In order to increase the number of identifiable models, it is desirable that a threshold be set to have a predetermined range on the basis of statistics of the obtained data group.

Figure 5:
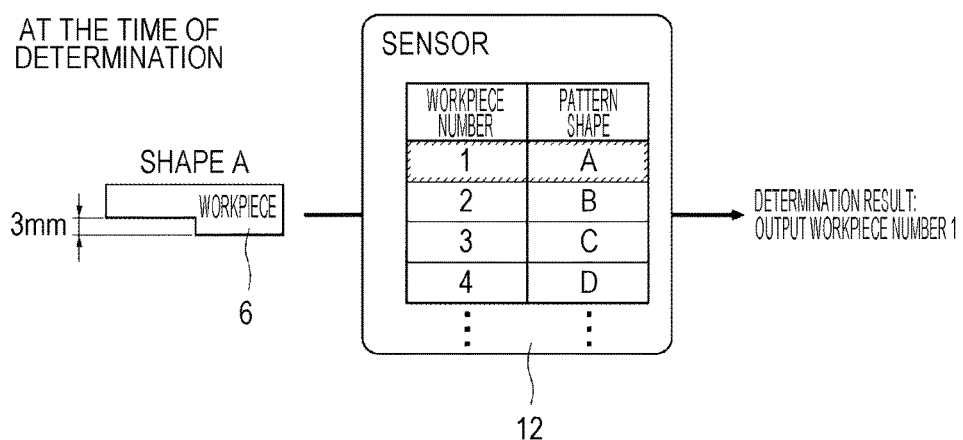
FIG. 5 is an explanatory view of identification of workpiece numbers in an embodiment.

FIG. 5 illustrates identification of workpiece numbers. Specifically, FIG. 5 is an explanatory view of an identification mode in which a cylinder block (workpiece 6) placed on the conveyance line is measured and is identified. As already described above, the workpiece 6 is measured. A differential value between values measured by the master sensor 1 and the slave sensor 2 is compared with the identification data table 12 to obtain a matched workpiece number. In a case where the matched workpiece number is the workpiece number 1, a result showing that the workpiece number is 1 is output to the machine tool controller 4. The machine tool controller 4 executes a processing instruction or the like based on the workpiece number 1.

The slave sensor 2 side of the identification shape that is the surface to be measured of the workpiece 6 protrudes toward the ultrasonic displacement sensor from the master sensor 1 side thereof by 3 mm. A workpiece number is allocated for each predetermined amount from this difference in level of 3 mm. For example, workpiece numbers are allocated at four stages so that each workpiece number is set per millimeter.

The cylinder block is a casting made by pouring metal into a mold. Therefore, it is impossible to achieve accuracy of 0.1 mm or 0.01 mm that a metal cut workpiece is required to have. Further, metal taken out from the mold is rough and uneven. For this reason, the predetermined amount for making a difference in level is approximately 0.7 to 1.4 mm and is desirably approximately 1 mm. With this, even in a case where the number of models to be identified is large, cylinder blocks are easily manufactured.

The workpiece number 1 is allocated to a difference in level of 3 mm, a workpiece number 2 is allocated to 4 mm, a workpiece number 3 is allocated to 2 mm, and a workpiece number 4 is allocated to 1 mm, whereby it is possible to identify four types of patterns having a protruding slave-sensor-2 side. At this time, it is desirable to allocate a workpiece number, which is allocated to a large number of models, to a value close to a set central value of the differences in level, instead of allocating workpiece numbers in order of size of the difference in level. In other words, in a case where workpieces of the model of the workpiece number 1 are manufactured in large amount, it is preferable to allocate the workpiece number 1 to 3 mm close to the central value of the differences in level. 3 mm is a central value in a case where five stages are set.

This is because higher reliability is obtained by distinguishing a large difference in level than by distinguishing a small difference in level. For example, higher reliability is obtained by identifying a difference in level between 3 mm and 5 mm than by identifying a difference in level between 5 mm and 4 mm. Because many models are allocated to the central value of the differences in level, it is possible to easily determine exceptions. For example, it is possible to easily determine exceptions when many models are allocated to 3 mm and an exceptional model is allocated to 5 mm.

Further, a master workpiece 11 having opposite unevenness is prepared as another pattern. Specifically, there is prepared a master workpiece 11 in which the master sensor 1 side protrudes from the slave sensor 2 side and the difference in level is similarly changed. With this, it is possible to identify 4×4=16 types of models. This makes it possible to reduce an input/output system between the master sensor 1 and the machine tool controller 4 to four bits (four bits can correspond to $2^4$=16 types). As a matter of course, in order to increase the number of models to be identified, the number of divisions of a difference in level may be increased. A pattern having no difference in level may be provided.

Figure 13:
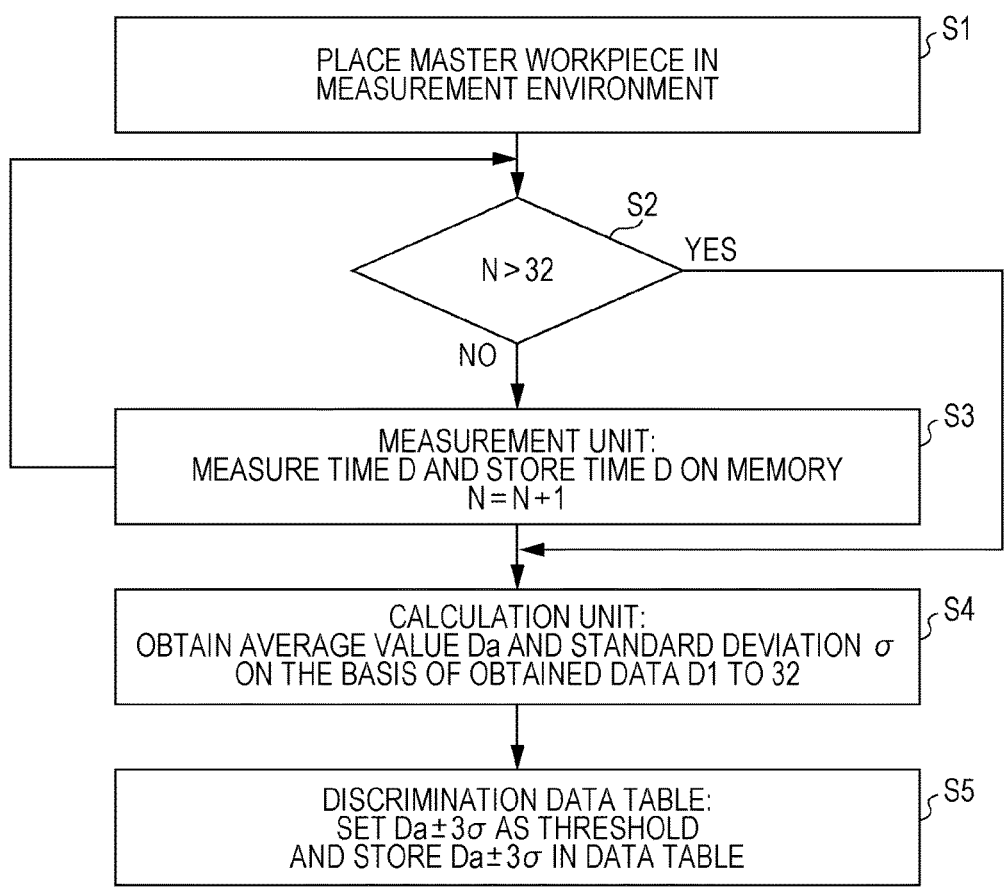
FIG. 13 is a flowchart of a method of setting a threshold in an embodiment.

FIG. 13 is a flowchart of a method of setting a threshold. The measurement unit measures the master workpiece 11 corresponding to each workpiece number a plurality of times. A calculation unit calculates a threshold for identifying a model. The threshold is set to have a range. First, the master workpiece 11, which is a reference of identification, is placed in an environment of executing model identification when, for example, a conveyance line of cylinder blocks is started to be operated. Next, a time D is repeatedly measured for a single master workpiece 11 corresponding to the workpiece number 1 a plurality of times per predetermined time, for example, thirty-two times per predetermined time (S2). The measured times D are stored in the memory 35 as a data group of times D1 to D32 (S3).

The calculation unit calculates an average value Da and a standard deviation σ on the basis of the times D1 to D32 serving as the obtained data group (S4). A threshold for the workpiece number 1 is set in the identification data table 12 so as to have ±3σ around the average value Da, in other words, Da±3σ (S5). The master sensor 1 and the slave sensor 2 transmit ultrasonic waves to the portion to be identified of the workpiece 6 placed on the conveyance line and receive reflected waves. When a difference between measurement values thereof falls within a range of the threshold set in the identification data table 12, an identification determination unit determines that the workpiece number of the workpiece 6 is 1. In a case where it is found that the workpiece number of the workpiece 6 is 1, the identification determination unit outputs a result showing that the workpiece number is 1 to the machine tool controller 4. The machine tool controller 4 executes a processing instruction or the like based on the workpiece number 1.

Figure 14:
FIG. 14 is a graph showing a state in which thresholds are allocated to respective workpiece numbers in an embodiment.

FIG. 14 is a graph showing a state in which thresholds are allocated to respective workpiece numbers. As an example, the workpiece number 1 to the workpiece number 6 are allocated by setting a difference in level to 1 mm. Six master workpieces 11 having different differences in level are prepared for the respective workpiece numbers. A data group, an average value Da, and a standard deviation σ thereof are calculated in accordance with FIG. 13. A threshold is set as a range indicated by a vertical line around the average value indicated by a black circle of each workpiece number. FIG. 4 shows that, in a case of a casting such as a cylinder block, set values can be sufficiently determined not to overlap with each other when the difference in level is set to approximately 0.7 to 1.4 mm, desirably to approximately 1 mm.

According to the above determination of the thresholds, each threshold is determined not only on the basis of a simple numerical value but also on the basis of a value measured by using the master workpiece 11 when the conveyance line of the workpiece 6 in an actual measurement environment is started to be operated. Further, variation in measurement values in the measurement environment and a statistical error are considered. Because of those points, the threshold does not have an excessive margin. Further, it is possible to correspond to a large number of models. Furthermore, it is possible to improve reliability.

Further, there have been described using an average value of a data group as the center. Instead of this, the most frequent value may be used as the center of thresholds. Furthermore, the standard deviation σ is obtained and then the average value Da±3σ is set in the identification data table 12. However, it is possible to employ ±σ or ±2σ, instead of ±3σ, depending on a numerical value distribution situation of the data group. Still further, there are learned a large number of measurement values obtained by using each master workpiece 11 a plurality of times, or a large number of measurement values of the workpiece 6, which are obtained at the time of identification and determination. Results thereof are set as empirical values. Determining thresholds and ranges on the basis of the empirical values is also effective.

Measurement values obtained by using ultrasonic waves are normally influenced by temperature. Not only this, but a beam size tends to be increased with respect to the workpiece 6 serving as an object to be measured. With this, an area to be measured is inevitably increased. In a case of cylinder blocks, an influence of a surface shape and roughness of castings is large. Therefore, the practical usage is difficult. Further, it is possible to reduce the beam size by providing an ultrasonic horn that is a reflector for converging and emitting ultrasonic waves in a certain direction or receiving ultrasonic waves. However, the ultrasonic horn can only receive sonic waves moving straight from the object to be measured. In view of this, it is desirable to use the fact that, in ultrasonic waves, the beam size can be reduced because straightness is increased in proportion to a magnitude of an oscillation frequency.

Further, in a case where frequencies are the same and dimensions of oscillators are different, directionality is increased when the dimension of the oscillator is large. In this case, a width of a beam is large in a short distance, whereas an ultrasonic wave beam is not much widened in a long distance. Meanwhile, when the dimension of the oscillator is small, directionality is reduced. In this case, a width of a beam is small in a short distance, whereas the beam is widened in a long distance. Therefore, reduction in echo height depending on a distance is remarkable.

Figure 6:
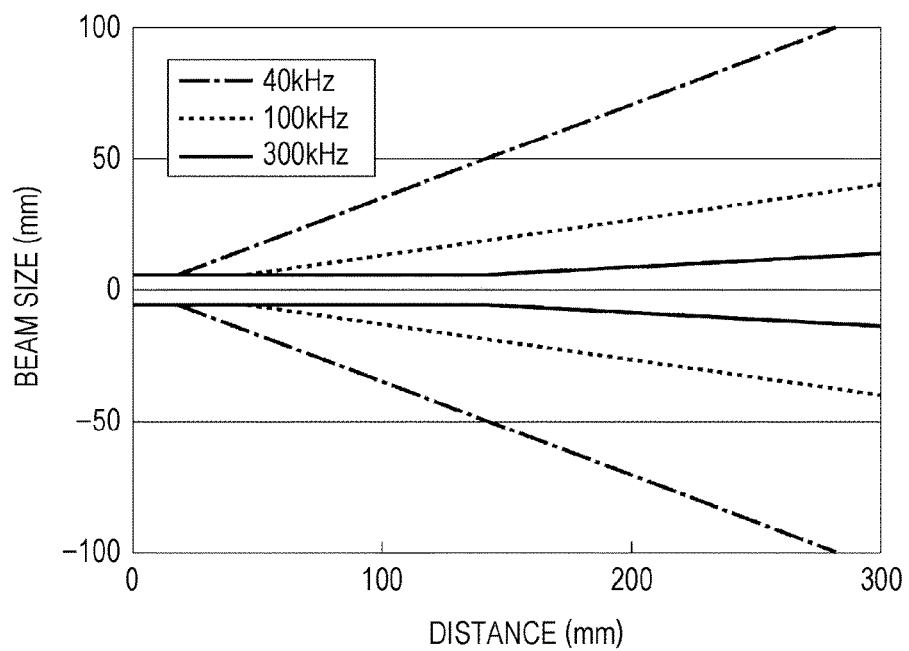
FIG. 6 is a graph of a relationship among a diameter of a beam spot, an oscillation frequency, and a distance of an ultrasonic displacement sensor.
Figure 7:
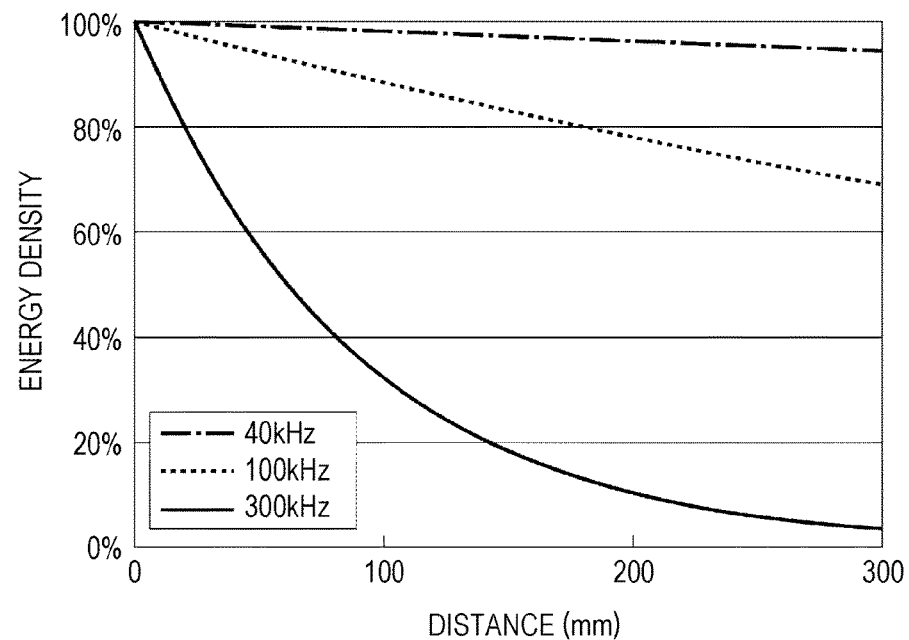
FIG. 7 is a graph of a relationship among an energy density, an oscillation frequency, and a distance of an ultrasonic displacement sensor.

FIG. 6 shows a relationship among a beam size, an oscillation frequency, and a distance of the ultrasonic displacement sensor. An alternate long and short dash line indicates 40 kHz, a broken line indicates 100 kHz, and a solid line indicates 300 kHz. Meanwhile, FIG. 7 shows a relationship among an energy density, an oscillation frequency, and a distance of the ultrasonic displacement sensor. As shown in the drawing, the energy density relating to an output intensity is attenuated as the oscillation frequency is higher. An alternate long and short dash line indicates 40 kHz, a broken line indicates 100 kHz, and a solid line indicates 300 kHz in the same way as in FIG. 6.

Figure 8:
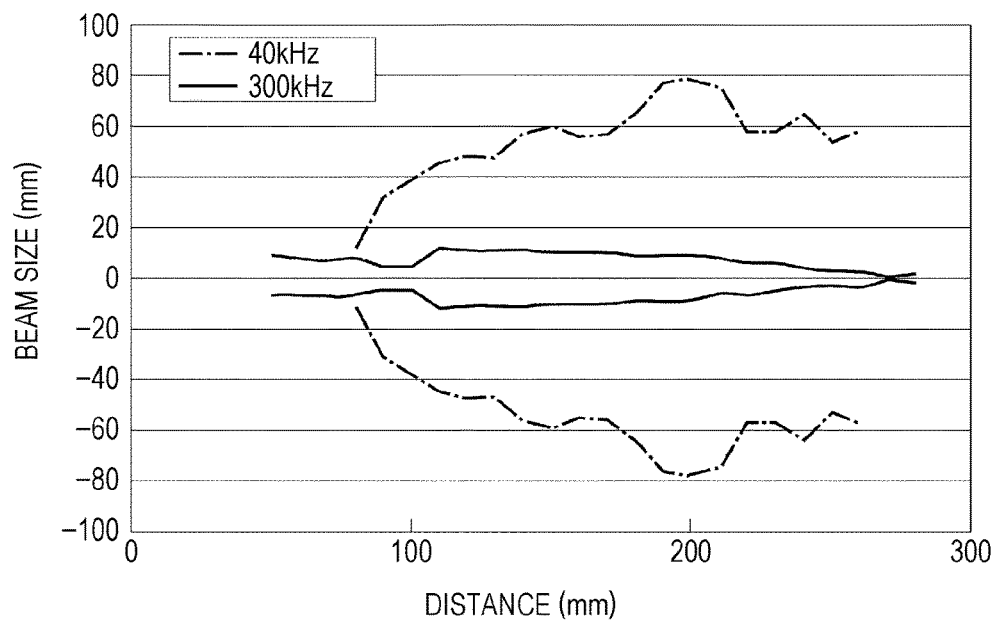
FIG. 8 is a graph of a relationship among a diameter of a beam spot, an oscillation frequency, and a distance of an ultrasonic displacement sensor according to an embodiment.

FIG. 8 shows actual measurement values of a beam size obtained in a case where the oscillation frequency is 40 kHz or 300 kHz. When the oscillation frequency is 300 kHz, it is possible to set a beam size to 20 mm corresponding to an appropriate area to be measured at an operation distance of 200 mm from the workpiece 6 (cylinder block) to the master sensor 1. Note that it is possible to set the oscillation frequency to 200 to 400 kHz, the operation distance to 150 to 250 mm, and the beam size to 15 to 25 mm that is a practical value for the cylinder block. Further, when a distance from the master sensor 1 and the slave sensor 2 to the portion to be identified is set to 150 to 200 mm, it is unnecessary to provide the sensors close to the portion to be identified in the manufacturing line of cylinder blocks. Therefore, it is easy to carry out position control for stopping the workpiece 6. Further, positions of the sensors do not hinder processing of the workpiece 6.

Further, the cylinder block is a casting. Thus, a difference in level of approximately 1 mm is prepared as a limit of unevenness of the surface to be measured. Meanwhile, in a case where the oscillation frequency is 40 kHz and the beam size is approximately 60 to 80 mm as in a typical ultrasonic displacement sensor, a resolution thereof is approximately 1 mm. Thus, it is impossible to measure a difference in level of 1 mm.

In a case where the oscillation frequency is 200 to 400 kHz and the operation distance is 150 to 250 mm, it is possible to improve the resolution up to approximately 0.1 mm. Thus, it is sufficiently possible to identify 1 mm that is a limit of making a difference in level in a casting even in consideration of an influence of surface roughness of the casting. Because the oscillation frequency of ultrasonic waves is 200 to 400 kHz, it is possible to reduce a beam size of ultrasonic waves and reduce an area of the portion to be identified. Further, because a beam size of ultrasonic waves to be transmitted at the portion to be identified is 15 to 20 mm, preparation of the portion to be identified is not hindered even in a casting having a complicated shape such as a cylinder block. However, when electric signals close to a resonance frequency of the ultrasonic elements 31 and 32 are applied to the ultrasonic elements 31 and 32 in a pulse, ultrasonic wave oscillation mechanically continues for a short time after the electric signals are not applied. When this phenomenon continues for a long time, detection becomes difficult because of a reflective type.

Figure 9:
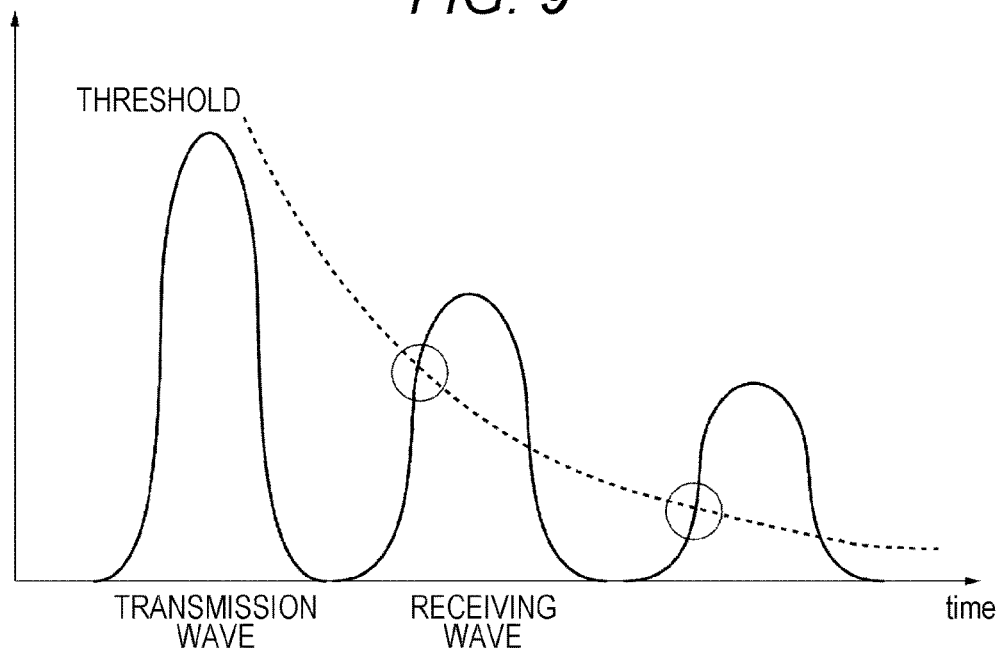
FIG. 9 is a graph of an output value to time in a typical ultrasonic displacement sensor.
Figure 10:
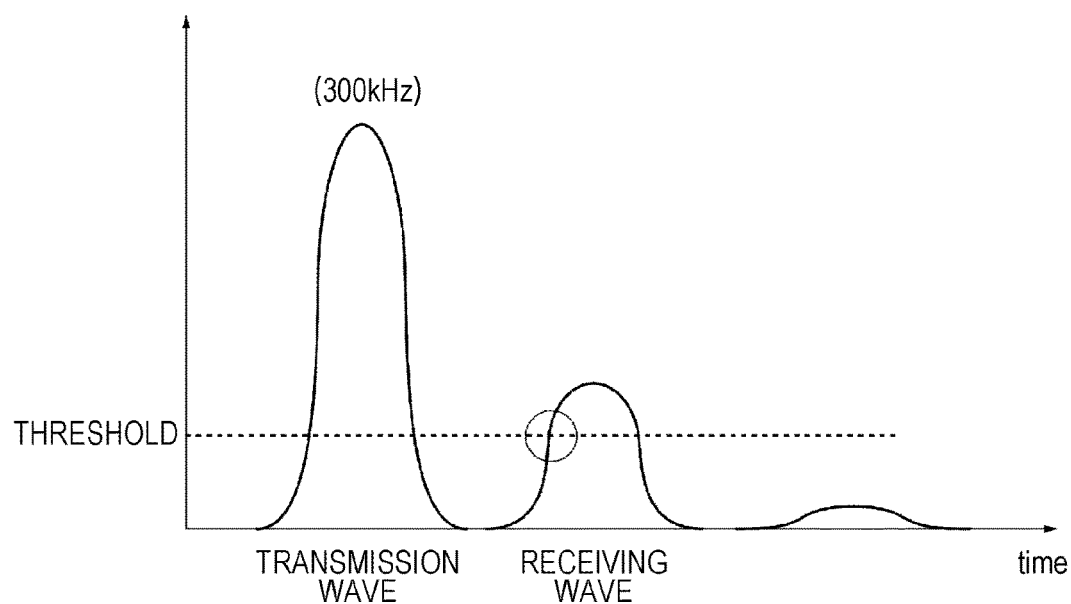
FIG. 10 is a graph of an output value to time in an ultrasonic displacement sensor according to an embodiment.

FIG. 9 shows a chronological change in output voltage from oscillation to reception in a case where the oscillation frequency is approximately 40 kHz as in typical one. Multi-reflected ultrasonic waves are detected at a peak on the rightmost side in a graph of FIG. 9. As described above, an attenuation amount of ultrasonic waves having a low frequency after transmission is small. Therefore, multiple reflection tends to occur. Thus, a typical ultrasonic distance measuring instrument may erroneously detect this multiple reflection. On the contrary, in a case where the oscillation frequency is 200 to 400 kHz, ultrasonic waves are largely attenuated. Therefore, reflected waves are also largely attenuated as indicated by a peak on the rightmost side in a graph of FIG. 10 (reflected waves are detected). Therefore, it is possible to reduce an influence of multiple reflection. This makes it possible to reduce variation in measurement.

Figure 11:
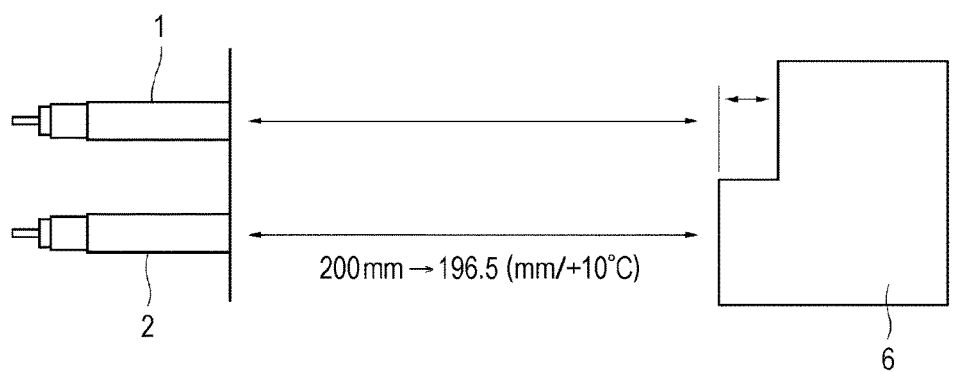
FIG. 11 is an explanatory view of an identification effect depending on a change in temperature, in an ultrasonic displacement sensor according to an embodiment.

FIG. 11 shows an identification effect depending on temperature in a case where the master sensor 1 and the slave sensor 2 are used as a single set. In a case where the temperature is increased by 10° C., a speed of sound is increased. Therefore, in a case where an increase in temperature of 10° C. is not corrected, a distance of 200 mm is measured as 196.5 mm. However, a difference is measured and is calculated, and therefore this influence can become negligibly small. A change in difference in level of 1 mm, which is caused by an increase in temperature of 10° C., is actually approximately 0.017 mm.

Figure 12:
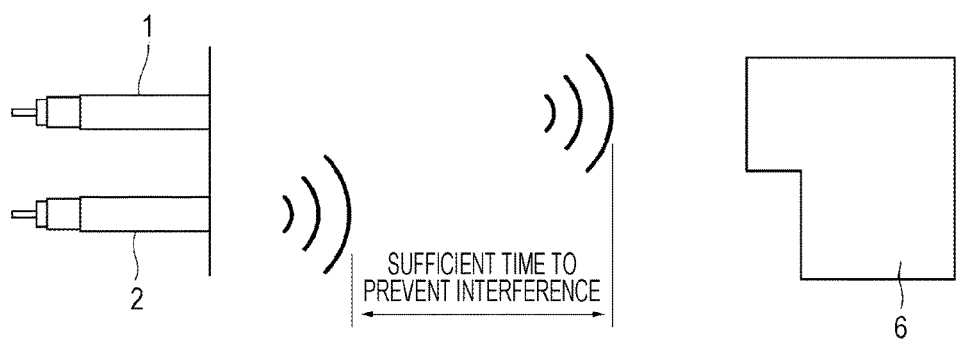
FIG. 12 is an explanatory view of a measurement interval in an ultrasonic displacement sensor according to an embodiment.

FIG. 12 shows timings at which, in a case where the master sensor 1 and the slave sensor 2 are used as a single set, both the sensors send ultrasonic waves. Oscillation of the slave sensor 2 is delayed from oscillation of the master sensor 1 by sufficient time to prevent two ultrasonic waves from interfering with each other. This time is longer than time taken to reciprocate over the operation distance of 200 mm. Further, ultrasonic waves are not simultaneously sent within this time. Furthermore, synchronization using a common clock is carried out to prevent the two timings from being shifted. Therefore, the CPUs 33 and 34 control each other. Further, in order to reduce variation in measurement values, it is desirable to repeat measurement 32 to 64 times for each identification. Further, it is desirable to stabilize the measurement by calculating a median value of repeated measurement values and excluding a remarkably different value with the use of, for example, a median filter.

Note that, in the above embodiment, a target to be identified is a casting. However, the target to be identified is not particularly limited as long as unevenness can be formed on the target. For example, it is also possible to integrally form a plastic molded article with the workpiece 6.

Figure 15:
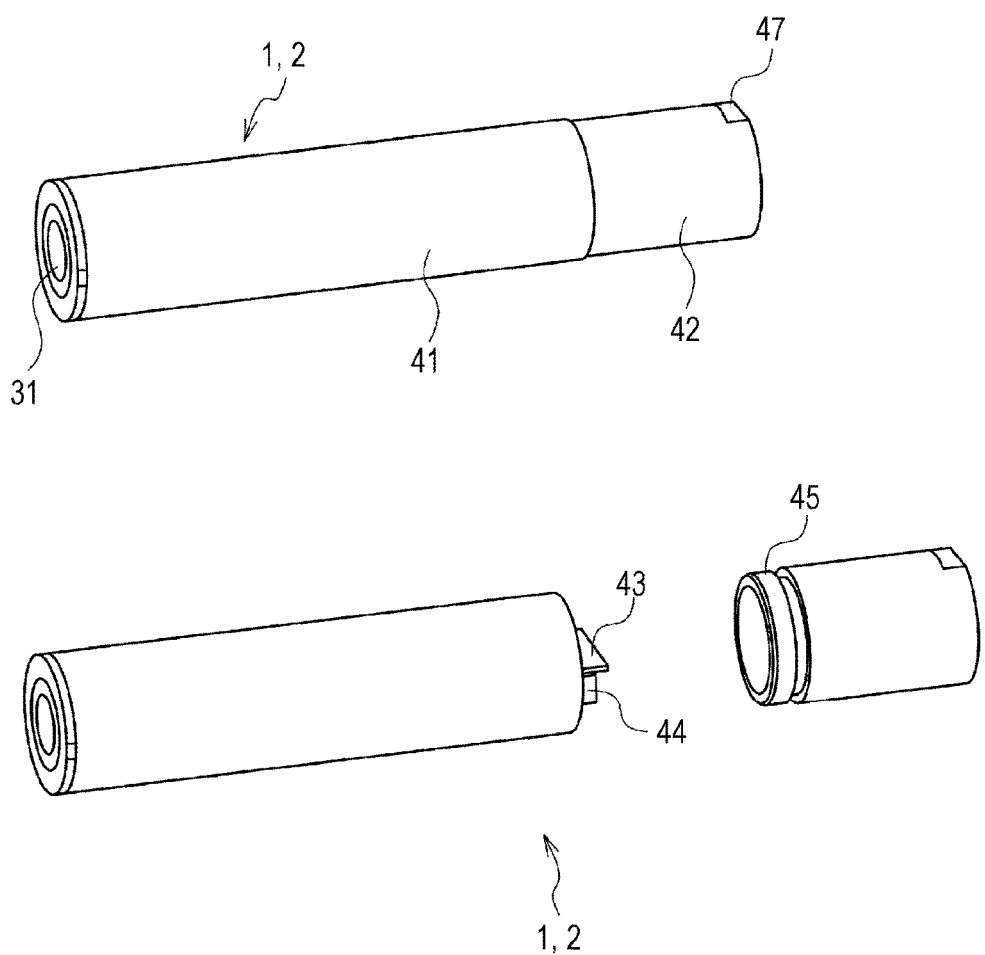
FIG. 15 is a perspective view of an external appearance of ultrasonic displacement sensors according to an embodiment.

FIG. 15 illustrates an external appearance of the master sensor 1 and the slave sensor 2 that are ultrasonic displacement sensors. A reference sign 41 denotes a main body case made of metal and including the ultrasonic element 31(32) at a left end. At the other right end, a transparent case 42 made of resin is thrust into the main body case 41 via a packing 45. A lower drawing shows a state in which the transparent case 42 is removed. A photoreflector 44 is placed at a position of the transparent case 42. The photoreflector 44 is a switch for switching the installation mode of the ultrasonic displacement sensor to the measurement mode thereof. A reference sign 43 denotes a substrate for operating the ultrasonic element 31 and the photoreflector 44. The substrate 43 protrudes toward the transparent case 42 side from the main body case 41. A reference sign 47 denotes an LED that shows a reception state of ultrasonic waves when the LED is turned on.

As described above, the ultrasonic displacement sensor according to the present invention desirably has a long (bar-like) shape. With this, this ultrasonic displacement sensor can have a compact shape. Therefore, a large space is unnecessary as a place to which this ultrasonic displacement sensor is attached. This is because, in a case where there is a gap, the ultrasonic displacement sensor can be installed by being inserted like a bar. Further, it is more preferable that the bar-like ultrasonic displacement sensor include the ultrasonic element 31 at one end and the transparent case 42 at the other end. This is because, with the above arrangement, the other end is the transparent case 42 functioning as a switch as described below when the end at which the ultrasonic element 31 is arranged is directed toward the target to be discriminated. With this, switching operation is easily carried out. Further, there is no possibility that the ultrasonic element 31 is blocked by a hand.

Figure 19:
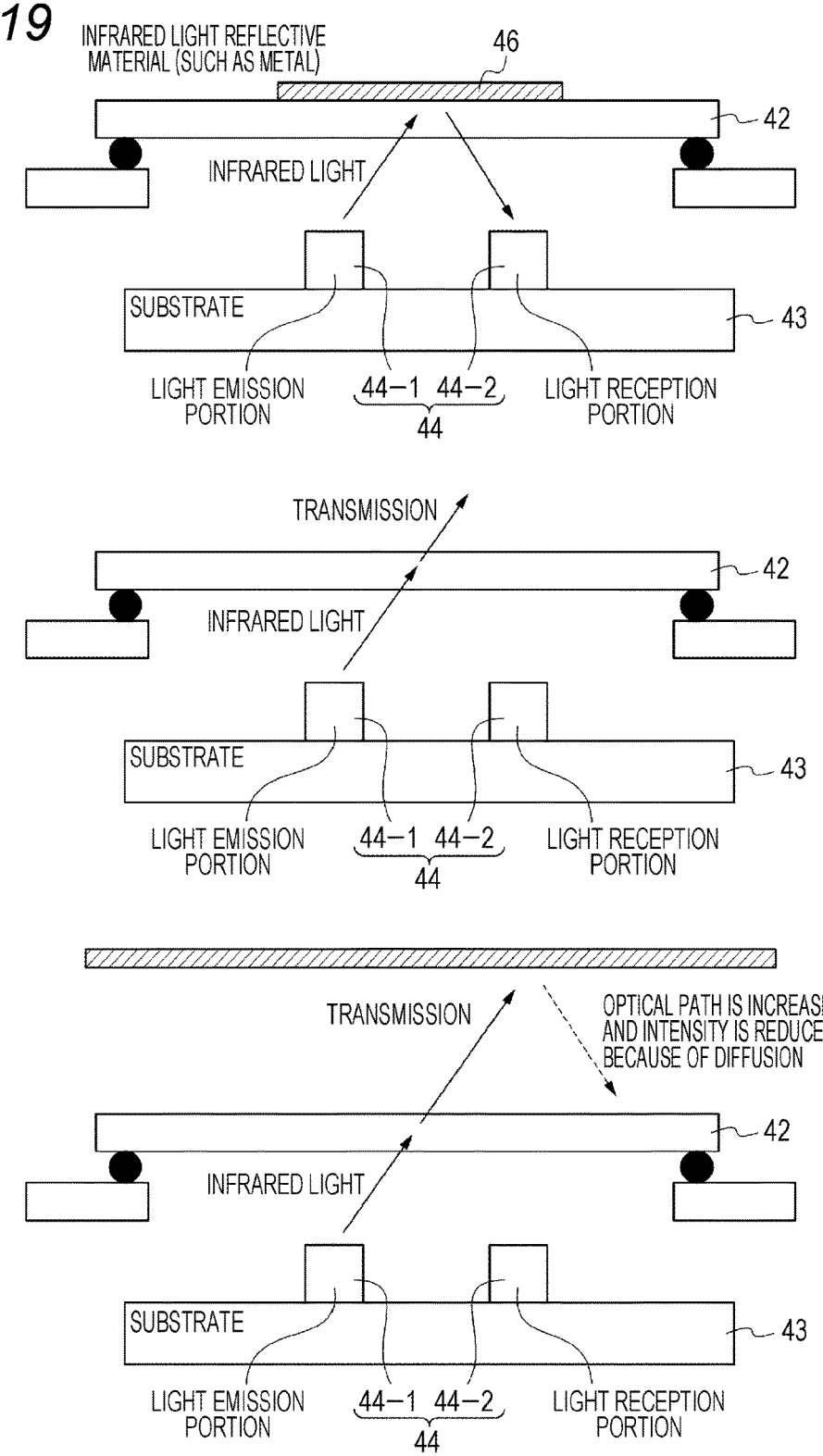
FIG. 19 is a cross-sectional view of details of a switching unit in an embodiment.

FIG. 19 is a cross-sectional view of details of a switching unit. A light emission portion 44-1 and a light reception portion 44-2 are provided on the substrate 43 as the photoreflector 44. An object blocking reflected light from the light emission portion 44-1 is detected by the light reception portion 44-2 to determine presence/absence of the object. A light emitting diode is normally used as a light emitting element for the light emission portion 44-1. As a countermeasure for ambient light, an infrared light emitting diode is desirably used. A phototransistor or an integrated circuit (photo IC) into which light reception portion is integrated is used as the light reception portion 44-2. The photoreflector 44 detects reflected light. Therefore, a structure of the photoreflector 44 tends to be influenced by ambient light. Thus, it is preferable to modulate light to identify the light from ambient light.

The transparent case 42 that can be considered transparent to infrared light is attached to the main body case 41 via the packing 45 on the outside of the photoreflector 44. With this, dustproof and waterproof effects are obtained by sealing the main body case 41. An upper drawing in FIG. 19 shows a state in which a reflective tape 46 is adhered to the outside of the transparent case 42, the reflective tape 46 being made of metal or the like and reflects infrared light. Thus, light from the light emission portion 44-1 passes through the transparent case 42, is reflected by the reflective tape 46, and arrives at the light reception portion 44-2.

A middle drawing in FIG. 19 shows a state in which the reflective tape 46 is removed. Light from the light emission portion 44-1 passes through the transparent case 42 but does not return to the light reception portion 44-2. A lower drawing in FIG. 19 shows that the reflective tape 46 or another reflective material is provided far from an outer surface of the transparent case 42. An optical path is increased, and therefore a light intensity arriving at the light reception portion 44-2 is reduced because of diffusion. Thus, when the state shown by the upper drawing in FIG. 19 is a switched-off state and the states shown by the middle drawing and lower drawing in FIG. 19 are a switched-on state, the switch-off state is the installation mode and the switched-on state is the measurement mode.

Figure 16:
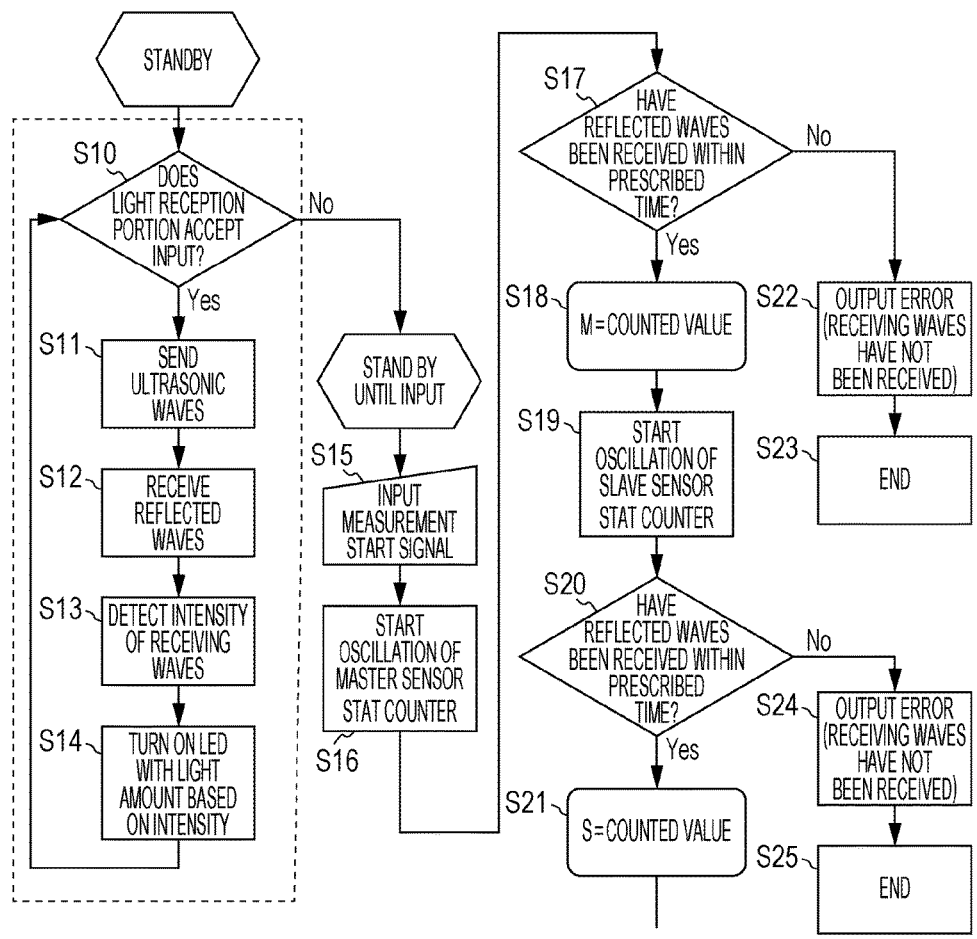
FIG. 16 is a flowchart of a flow from an installation mode to a measurement mode in an embodiment.
Figure 17:
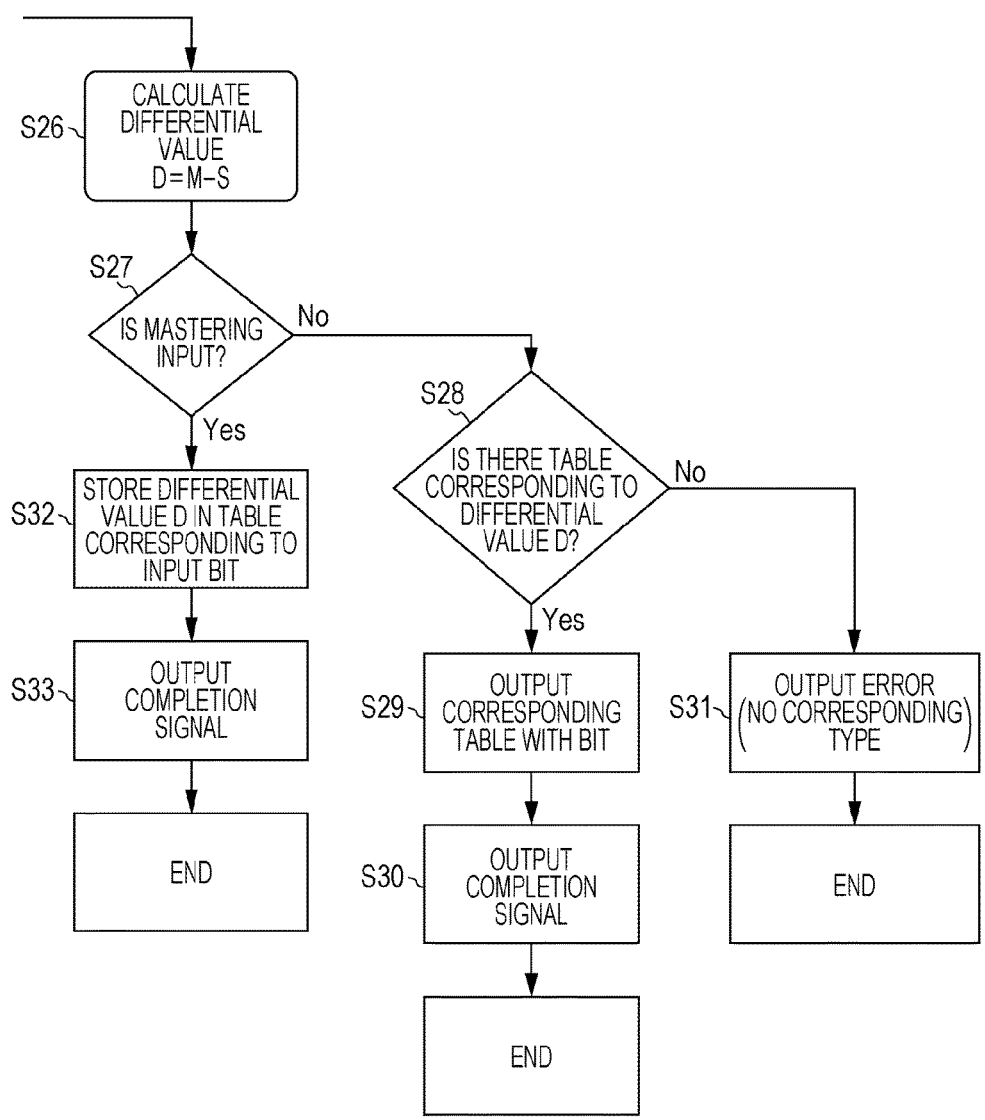
FIG. 17 is a flowchart of a flow from an installation mode to a measurement mode in an embodiment (continuation from FIG. 16).
Figure 18:
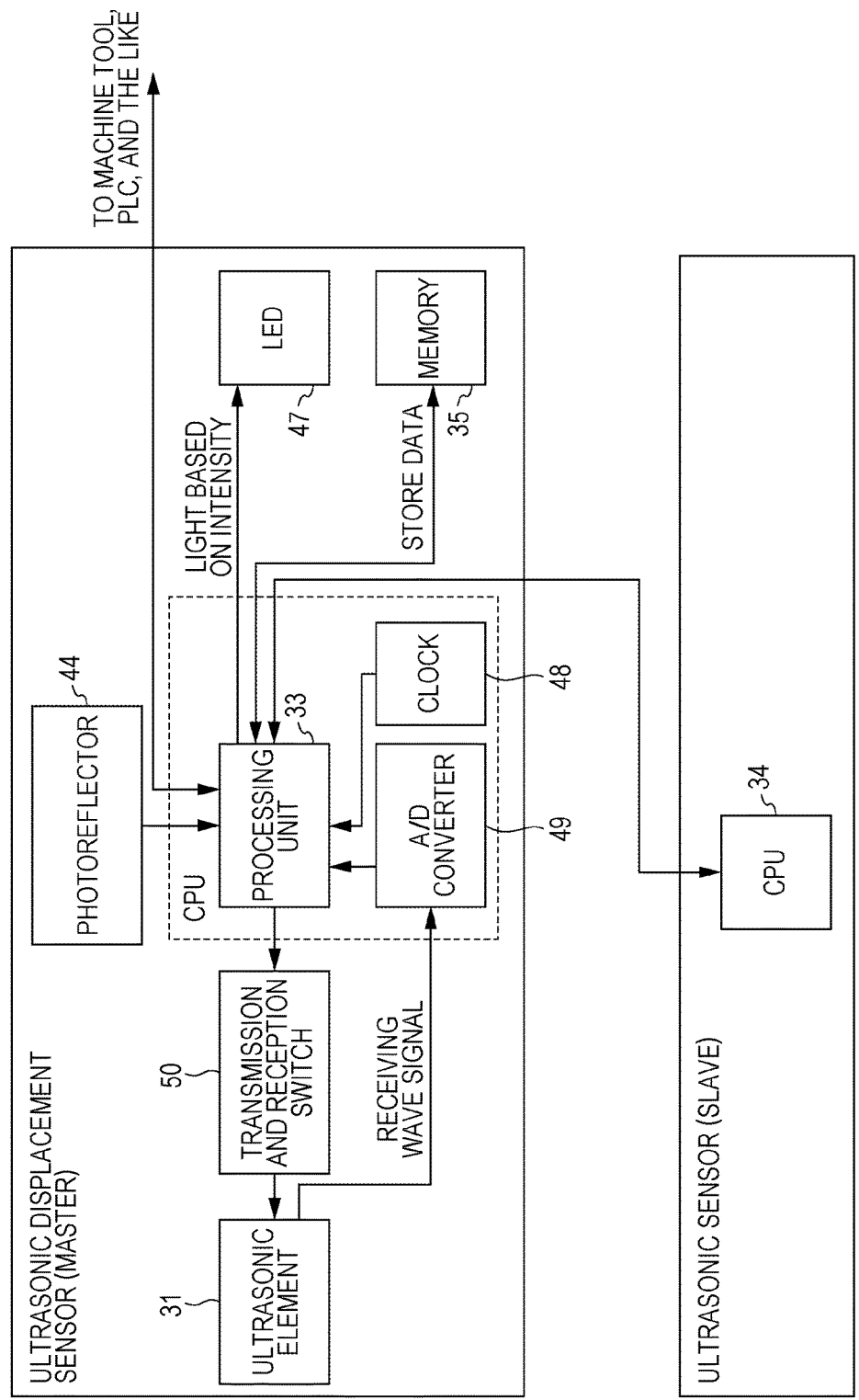
FIG. 18 is a block diagram relating to switching from an installation mode to a measurement mode in an embodiment.

FIGS. 16 and 17 are flowcharts of a flow from the installation mode to the measurement mode. FIG. 18 is a block diagram relating thereto. First, a part surrounded by a broken-line frame border is the installation mode. This is a state in which the reflective tape 46 is adhered to the transparent case 42. This means that the light reception portion 44-2 receives input. In the installation mode, an operator who carries out position adjustment adjusts an attachment position of the ultrasonic displacement sensor, in other words, an attachment position of the main body case 41 so as to increase a reception intensity of ultrasonic waves.

The CPU 33 determines whether or not the light reception portion 44-2 receives input (S10). In a case where there is input, the mode is the installation mode. Thus, a transmission and reception switch 50 is switched for position adjustment, and the ultrasonic element 31 sends ultrasonic waves (S11). Further, the ultrasonic element 31 receives reflected waves (S12). The received reflected waves are digitally converted by an A/D converter 49 forming an intensity detection unit, are then input to the CPU 33, and are detected as an intensity (S13). The CPU 33 turns on the LED 47 so that the LED 47 has a light amount based on the intensity (S14). Therefore, an operator who carries out position adjustment only needs to visually recognize brightness of the LED 47 and fix a position of the main body case 41 to a place at which the LED 47 emits the brightest light. Then, this operator fixes the position and then removes the reflective tape 46 from the transparent case 42. At this time, a shock applied to the main body case 41 is such force as to remove the reflective tape 46. This makes it possible to eliminate a shift of the position of the ultrasonic displacement sensor caused by the shock.

When the reflective tape 46 is removed and nothing is input to the light reception portion 44-2, a mode switching unit of the CPU 33 sets the mode to the measurement mode. In the measurement mode, a measurement start signal is input to the master sensor 1 from the machine tool controller 4 (S15). The master sensor 1 starts oscillation, and a counter of time is started (S16). The CPU 33 determines whether or not reflected waves have been received within a prescribed time (S17). When reflected waves are received, a counted value M from oscillation to reception carried out by the master sensor 1 is stored in the memory 35 (S18). Next, the CPU 33 similarly starts oscillation of the slave sensor 2 (S19). Whether or not reflected waves have been received within a prescribed time is determined (S20). When reflected waves are received, a counted value S from oscillation to reception carried out by the slave sensor 2 is stored (S21). The ultrasonic element 32 of the slave sensor 2 oscillates to synchronize with a signal of a clock 48 provided on the master sensor 1 side. In any case, when reflected waves cannot be received within the prescribed time, an error occurs (S22, S24). Then, the measurement is halted and the end of the measurement is displayed (S23, S25).

The master sensor 1 calculates a differential value D, as M-S, between the measurement data of the master sensor 1 stored in the memory 35 and the measurement data output from the slave sensor 2 (S26). Thereafter, the CPU 33 determines whether or not the mode is the mastering mode (S27). In a case where the mode is not the mastering mode, the mode is the identification mode. Therefore, whether or not the differential value D is in the identification data table 12 is determined (S28). In a case where the differential value D is in the identification data table 12, the differential value D is referred to in the identification data table 12 to obtain a matched workpiece number. This workpiece number is output with a corresponding bit (S29). Then, a completion signal is output (S30). In a case where there is no matched workpiece number in the identification data table 12, an error, i.e., no corresponding type is output (S31).

In a case where the mode is the mastering mode (a mastering signal is input), the differential value D between the values read by the master sensor 1 and the slave sensor 2 is stored (S32). The differential value D is associated with a workpiece number. The workpiece number is registered in the identification data table 12 serving as a reference of identification. A completion signal is output (S33).

As described above, the transparent case 42 and the photoreflector 44 are provided in the main body case 41 of each of the master and slave sensors 1 and 2 that are ultrasonic displacement sensors. Therefore, presence/absence of the reflective tape 46 detected by the photoreflector 44 can be used as a switch for switching between the installation mode and the measurement mode. Further, the photoreflector 44 is completely included in the transparent case 42 unlike a switch having a machine mechanism, the switch being inferior in terms of waterproof and dustproof effects. Further, the transparent case 42 is attached to the main body case 41 via the packing 45. Therefore, those ultrasonic displacement sensors can be sensors having sufficient waterproof and dustproof effects.

The transparent case 42 only needs to be transparent to infrared light, and therefore the switch can be sufficiently operated with transparency of frosted glass. Further, because the switch has its own light source, stable operation can be achieved even in a dark part inside the machine or inside the apparatus. Furthermore, even in a case where the transparent portion is covered by liquid, dust, or the like, the liquid, dust, or the like does not reflect infrared light. Therefore, this does not lead to a malfunction of the switch. Still further, adjustment and the like, for setting a responding distance of the ultrasonic displacement sensor, of a position, a gain, and a threshold is carried out in a place sufficiently far from the main body case 41. Therefore, no reaction to a reflective article such as a wall occurs. Further, no malfunction occurs even on a conveyance line or the like on which miscellaneous objects are placed.

OTHER EMBODIMENTS

The present invention also includes the following embodiments.

According to the following embodiments, a master workpiece, which is a reference of measurement and corresponds to a model of a workpiece, is placed on the conveyance line. The master workpiece is measured by an ultrasonic displacement sensor a plurality of times. A threshold for identifying a model is obtained on the basis of measured values. Therefore, measurement is not influenced by, in particular, a measurement environment such as temperature, oil mist, or dust. This makes it possible to securely identify a large number of models of workpieces. A plurality of models is accurately identified on, in particular, a conveyance line of cylinder blocks in a manufacturing facility of engines for automobiles to improve reliability.

Another Embodiment 1

A workpiece identification apparatus for identifying a model of a workpiece placed on a conveyance line and having a portion to be identified at a predetermined position, the workpiece identification apparatus including:

an ultrasonic displacement sensor configured to transmit ultrasonic waves to the portion to be identified, receive reflected waves, and measure time between transmission and reception; and a master workpiece serving as a reference of the measurement and corresponding to the model, in which the master workpiece is placed on the conveyance line, the placed master workpiece is measured by the ultrasonic displacement sensor a plurality of times, and a threshold for identifying the model is set on the basis of measured values.

Another Embodiment 2

A workpiece identification apparatus for identifying a model of a workpiece placed on a conveyance line and having a portion to be identified at a predetermined position, the workpiece identification apparatus including:

a master sensor and a slave sensor configured to transmit ultrasonic waves to the portion to be identified, receive reflected waves, and measure time between transmission and reception;

a master workpiece serving as a reference of the measurement and corresponding to the model;

a measurement unit configured to place the master workpiece on the conveyance line and measure the placed master workpiece a plurality of times by using the master sensor and the slave sensor;

a memory configured to store a difference between values measured the plurality of times as a data group;

a calculation unit configured to obtain a threshold for identifying the model on the basis of the data group;

an identification data table for storing the threshold obtained by the calculation unit; and an identification determination unit configured to measure the portion to be identified of the workpiece by using the master sensor and the slave sensor, compare the difference between the measured values with the threshold stored in the identification data table, and identify the model of the workpiece.

Another Embodiment 3

The workpiece identification apparatus according to another embodiment 1 or 2, in which the threshold is set to have a predetermined range on the basis of statistics of the values measured the plurality of times.

Another Embodiment 4

The workpiece identification apparatus according to any one of other embodiments 1 to 3, in which the threshold is set to have a predetermined range on the basis of an average value and a standard deviation of the values measured the plurality of times.

Another Embodiment 5

The workpiece identification apparatus according to another embodiment 4, in which the range is a range shown by the average value ±(3× the standard deviation).

Another Embodiment 6

The workpiece identification apparatus according to any one of other embodiments 2 to 5, in which the master sensor and the slave sensor are arranged at a position facing the portion to be identified and identify the model by detecting a difference in level between a surface of the portion to be identified facing the master sensor and a surface of the portion to be identified facing the slave sensor.

Another Embodiment 7

A workpiece identification method for identifying a model of a workpiece on a conveyance line, the workpiece identification method including placing a master workpiece on the conveyance line, the master workpiece serving as a reference and corresponding to the model, measuring the placed master workpiece a plurality of times by using an ultrasonic displacement sensor, and obtaining a threshold, on the basis of measured values, for identifying the model.

Another Embodiment 8

A workpiece identification method for identifying a model of a workpiece on a conveyance line, the workpiece identification method including placing a master workpiece, on the conveyance line, the master workpiece serving as a reference and corresponding to the model, measuring the placed master workpiece a plurality of times by using a master sensor and a slave sensor, storing a difference between values measured the plurality of times as a data group, obtaining a threshold, on the basis of the data group, for identifying the model storing the obtained threshold in an identification data table, comparing the threshold stored in the identification data table with a value obtained by measuring a portion to be identified of the workpiece by using the master sensor and the slave sensor, and identifying the model of the workpiece.

DESCRIPTION OF REFERENCE SIGNS

1 Master sensor
2 Slave sensor
3 Sensor unit
4 Machine tool controller
5 Machine tool
6 Workpiece
11 Master workpiece
12 Identification data table
31, 32 Ultrasonic element
33, 34 CPU
35, 36 Memory
41 Main body case
42 Transparent case
43 Substrate
44 Photoreflector
44-1 Light emission portion
44-2 Light reception portion
45 Packing
46 Reflective tape
47 LED
48 Clock
49 A/D converter
50 Transmission and reception switch

The invention claimed is:

1. An ultrasonic displacement sensor for transmitting ultrasonic waves to an object, receiving reflected waves, and measuring time between transmission and reception, the ultrasonic displacement sensor comprising:
   a main body case including an ultrasonic element at an end;
   a transparent case attached to the main body case;
   a photoreflector provided at a position of the transparent case and including a light emission portion and a light reception portion; and
   a switching unit configured to switch, on the basis of output from the photoreflector, between an installation mode in which an attachment position of the main body case is adjusted and a measurement mode in which the object is measured.

2. The ultrasonic displacement sensor according to claim 1, comprising
   an LED configured to be turned on to have a light amount based on an intensity of received reflected waves.

3. The ultrasonic displacement sensor according to claim 2, comprising:
   an ultrasonic element configured to transmit ultrasonic waves and receive reflected waves when the light reception portion accepts input; and an intensity detection unit configured to detect an intensity of received reflected waves.

4. The ultrasonic displacement sensor according to claim 2, wherein the transparent case is attached to the main body case via a packing.

5. The ultrasonic displacement sensor according to claim 2, wherein
   the transparent case is provided at another end that is an opposite side of the end at which the ultrasonic element is placed.

6. The ultrasonic displacement sensor according to claim 1, comprising:
   an ultrasonic element configured to transmit ultrasonic waves and receive reflected waves when the light reception portion accepts input; and an intensity detection unit configured to detect an intensity of received reflected waves.

7. The ultrasonic displacement sensor according to claim 6, wherein the transparent case is attached to the main body case via a packing.

8. The ultrasonic displacement sensor according to claim 6, wherein
   the transparent case is provided at another end that is an opposite side of the end at which the ultrasonic element is placed.

9. The ultrasonic displacement sensor according to claim 1, wherein
   the transparent case is attached to the main body case via a packing.

10. The ultrasonic displacement sensor according to claim 9, wherein
    the transparent case is provided at another end that is an opposite side of the end at which the ultrasonic element is placed.

11. The ultrasonic displacement sensor according to claim 1, wherein
    the transparent case is provided at another end that is an opposite side of the end at which the ultrasonic element is placed.

* * * * *